(12) United States Patent
Feinbloom et al.

(10) Patent No.: US 10,061,115 B2
(45) Date of Patent: Aug. 28, 2018

(54) MAGNIFICATION DEVICE AND ASSEMBLY

(71) Applicants: Richard E. Feinbloom, New York, NY (US); Kenneth Braganca, Sayville, NY (US); Margaret Burns, Northport, NY (US)

(72) Inventors: Richard E. Feinbloom, New York, NY (US); Kenneth Braganca, Sayville, NY (US); Margaret Burns, Northport, NY (US)

(73) Assignee: Designs for Vision, Inc., Bohemia, NY (US)

( * ) Notice: Subject to any disclaimer, the term of this patent is extended or adjusted under 35 U.S.C. 154(b) by 706 days.

(21) Appl. No.: 14/051,446

(22) Filed: Oct. 11, 2013

(65) Prior Publication Data
US 2014/0036356 A1    Feb. 6, 2014

Related U.S. Application Data

(63) Continuation-in-part of application No. 13/065,809, filed on Mar. 30, 2011, now abandoned.

(51) Int. Cl.
*G02B 5/22* (2006.01)
*G02B 27/02* (2006.01)
(Continued)

(52) U.S. Cl.
CPC ............ *G02B 25/007* (2013.01); *G02B 5/22* (2013.01); *G02B 5/26* (2013.01); *G02B 25/004* (2013.01); *G02B 27/027* (2013.01)

(58) Field of Classification Search
CPC . G02B 1/00; G02B 1/041; G02B 5/00; G02B 5/003; G02B 5/20; G02B 5/206; G02B 5/208; G02B 5/22; G02B 5/223; G02B 5/24; G02B 5/26; G02B 5/28; G02B 5/281; G02B 5/282; G02B 5/283; G02B 7/00; G02B 23/00; G02B 23/12; G02B 23/125; G02B 23/14; G02B 25/00; G02B 25/002; G02B 25/004; G02B 25/005;
(Continued)

(56) References Cited

U.S. PATENT DOCUMENTS 2,986,969 A *  6/1961  Muncheryan .......... G02B 7/002
                                                351/49
3,273,456 A    9/1966  Feinbloom
(Continued)

*Primary Examiner* — Thong Nguyen
(74) *Attorney, Agent, or Firm* — Law Office of Carl A. Giordano, PA

(57) ABSTRACT

A magnification device including a housing having a distal open end and a proximal open end is disclosed. The housing includes an optical system including one or more objective lenses adjacent the distal open end, and one or more eye lenses adjacent the proximal open end, the optical system produced a desired level of magnification; and a filtering system having first filter selectively filtering a first group of wavelengths and a second filter selective filtering a second group of wavelengths. The first and second filters having an optical density selected based on a magnification level of the optical system. A vision enhancing assembly including a carrier device and one or more magnification devices coupled to the carrier device is also disclosed, wherein the magnification devices include filters that have optical densities based on a magnification level.

16 Claims, 6 Drawing Sheets

(51) Int. Cl.
*G02B 25/00* (2006.01)
*G02B 5/26* (2006.01)

(58) Field of Classification Search
CPC .... G02B 25/007; G02B 27/006; G02B 27/02; G02B 27/021; G02B 27/022; G02B 27/025; G02B 27/027
See application file for complete search history.

(56) References Cited

U.S. PATENT DOCUMENTS

| | | | | |
|---|---|---|---|---|
| 3,519,339 A | * | 7/1970 | Hutchinson | A61F 9/022 351/159.63 |
| 4,089,117 A | * | 5/1978 | Villarreal | F41G 1/38 359/611 |
| 4,511,225 A | * | 4/1985 | Lipson | A61F 9/022 2/432 |
| 5,162,647 A | * | 11/1992 | Field, Jr. | H01J 29/898 250/214 VT |
| 7,286,287 B1 | | 10/2007 | Ofne | |
| 7,477,451 B2 | * | 1/2009 | Katz | G02B 3/0037 359/399 |
| 7,532,394 B2 | * | 5/2009 | Gebelein | G02B 23/12 359/407 |
| 2007/0053540 A1 | | 3/2007 | Harvey | |
| 2008/0219654 A1 | * | 9/2008 | Border | H04N 5/23212 396/89 |
| 2010/0053540 A1 | | 3/2010 | Blayden | |
| 2011/0270035 A1 | * | 11/2011 | Gono | A61B 1/00096 600/118 |

\* cited by examiner

MAGNIFICATION DEVICE AND ASSEMBLY

CLAIM OF PRIORITY

This application claims, pursuant to 35 USC 120, priority to, and the benefit of the earlier filing date, as a continuation-in-part, to that application entitled "Magnification Device and Assembly," filed on Mar. 30, 2011 and afforded Ser. No. 13/065,809 (now abandoned) the entire contents of which are incorporated, herein, by reference.

BACKGROUND OF THE INVENTION

Field of the Invention

The invention relates generally to optical devices, and more particularly, to optical magnification devices for use in the presence of a source of electromagnetic radiation.

Background Information

Lasers have found utility in a number of applications, including, for example, communications, energy production, electronics, cosmetology, dermatology, medicine, and dentistry. Light (or electromagnetic radiation) emitted from a laser, predominantly by stimulated emission, is extremely intense, coherent, monochromatic, and highly collimated. When a laser is used, for example, during a medical or dental procedure, the surgeon or dentist must wear an eye protection device, for example, laser safety glasses, to avoid damage to the eye, as the beam produced by the laser can cause significant damage to the eye.

In addition to lasers, magnification devices may be also used, for example, by surgeons and dentists during medical or dental procedures, for magnifying a work area requiring precision. The magnification devices used may include telescopes, microscopes, endoscopes, and eye-loupes.

Exposure to laser beams in the visible (400 nm to 700 nm) and near-infrared (700 nm to 1400 nm) regions of the spectrum (retinal hazard region) may damage the retina, particularly when viewed through magnifying optical devices, as the energy concentration of a laser beam may increase up to one million times. Although infrared lasers (1.400 pm to 1 mm) and ultraviolet lasers 0.180 pm to 0.400 pm) do not present a retinal hazard, damage to the eye can still occur.

Currently available laser safety glasses or goggles filter out the wavelength or wavelengths emitted by the laser, with the goal of providing maximum visible light transmission (VLT). To filter out the wavelength, chemical additives or dyes or thin films may be added to a filter (in the form of a lens), which may be formed of polycarbonate, glass, or other suitable material, to match and consequently absorb the wavelength and power of the source of laser radiation. In addition to absorptive, reflective filters may also be used.

Depending upon the laser and the application, the attenuation or optical density (OD) of the filter lens at a specific wavelength should be specified. Since lasers may radiate at more than one wavelength, eyewear designed to have an adequate OD of a particular wavelength may have an inadequate OD at another wavelength for light emitted by the same laser. Most eye protection glasses or goggles use selective wavelength attenuation to protect eyes from harmful laser radiation while permitting the eyes to see something of interest, by filtering radiation inside and outside the visible range, yet many of the currently-available devices are cumbersome or uncomfortable when used in conjunction with an optical magnifying device.

Accordingly, there remains a need for optical magnification devices suitable for use in the presence of a radiation-emitting source to protect the eyes of a user.

SUMMARY OF THE INVENTION

Briefly described, according to an aspect of the invention, a magnification device includes a housing including a distal open end and a proximal open end; an optical system including one or more objective lenses mounted in the housing adjacent the distal open end, and one or more eye lenses mounted in the housing adjacent the proximal open end, achieving a desired level of magnification; and a filtering system comprising a first filter lens mounted to the distal open end of the housing adjacent and a second filter lens mounted to the proximal open end adjacent the one or more eye lenses, the first and second filter lens having first and second optical densities, respectively, selected based on the desired level of magnification.

According to another aspect of the invention, a vision enhancing assembly includes a carrier device; one or more magnification devices coupled to the carrier device, each of the magnification devices including: a housing including a distal open end and a proximal open end; an optical system including one or more objective lenses mounted in the housing adjacent the distal open end, and one or more eye lenses mounted in the housing adjacent the proximal open end, the optical system achieving a desired level of magnification; and a filtering system having first and second filtering lens, each having an optical density based on the desired level of magnification.

BRIEF DESCRIPTION OF THE DRAWINGS

The advantages, nature, and various additional features of the invention will appear more fully upon consideration of the illustrative embodiments now to of the described in detail in connection with accompanying drawings where like reference numeral to identify like element throughout the drawings.

It is noted that the drawings of the invention are not to scale. The drawings are intended to depict only typical aspects of the invention, and therefore should not be considered as limiting the scope of the invention. In the drawings, like numbering represents like elements between the drawings.

It is to be understood that the figures and descriptions of the present invention described herein have been simplified to illustrate the elements that are relevant for a clear understanding of the present invention, while eliminating, for purposes of clarity many other elements. However, because these omitted elements are well-known in the art, and because they do not facilitate a better understanding of the present invention, a discussion of such element is not provided herein. The disclosure herein is directed to also variations and modifications known to those skilled in the art.

DETAILED DESCRIPTION OF THE INVENTION

As used herein, the terms "comprises", "comprising", "includes", "including", "has", "having", or any other variation thereof, are intended to cover non-exclusive inclusions. For example, a process, method, article or apparatus that comprises a list of elements is not necessarily limited to only those elements but may include other elements not expressly listed or inherent to such process, method, article, or apparatus. In addition, unless expressly stated to the contrary, the term "of" refers to an inclusive "or" and not to an exclusive "or". For example, a condition A or B is satisfied by any one of the following: A is true (or present) and B is false (or not present); A is false (or not present) and B is true (or present); and both A and B are true (or present).

The terms "a" or "an" as used herein are to describe elements and components of the invention. This is done for convenience to the reader and to provide a general sense of the invention. The use of these terms in the description herein should be read and understood to include one or at least one. In addition, the singular also includes the plural unless indicated to the contrary. For example, reference to a composition containing "a compound" includes one or more compounds. As used in this specification and the appended claims, the term "or" is generally employed in its sense including "and/or" unless the content clearly dictates otherwise.

All numeric values are herein assumed to be modified by the term "about," whether or not explicitly indicated. The term "about" generally refers to a range of numbers that one of skill in the art would consider equivalent to the recited value (i.e., having the same function or result). In any instances, the terms "about" may include numbers that are rounded (or lowered) to the nearest significant figure.

Figure 1:
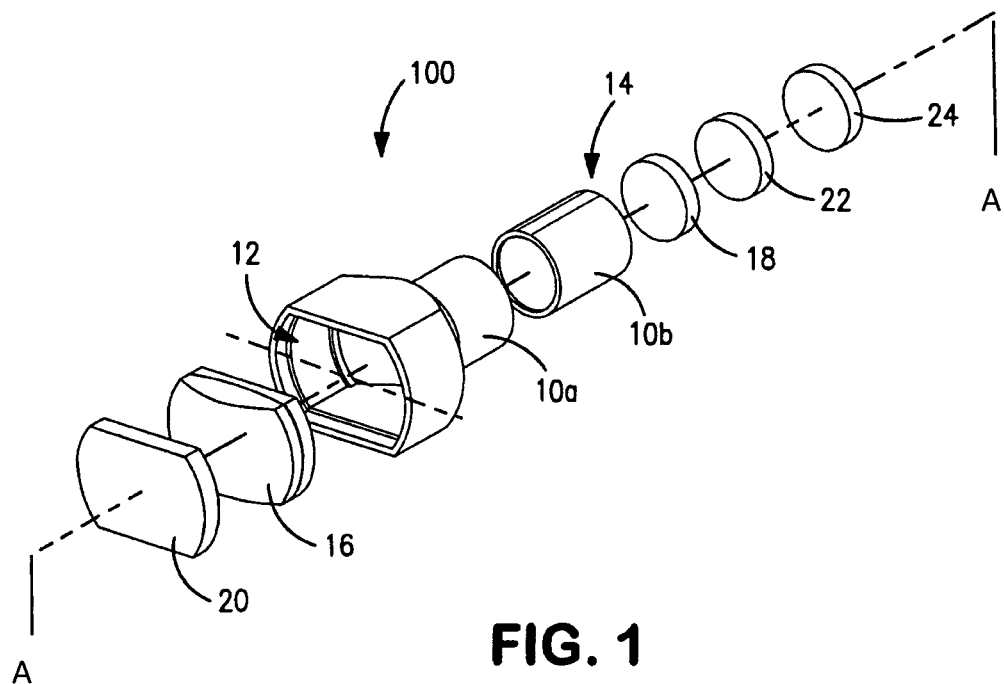
FIG. 1 is an exploded perspective view of a first embodiment of a magnification device according to an aspect of the invention.

Referring to FIG. 1, a magnification device 100 according to an aspect of the invention is illustrated. Separate housing portions 10a and 10b are provided to allow for the precise placement of the objective lens(es) 16 and the eye lens(es) 18 prior to assembly. The housing portions 10a and 10b are formed of a relatively rigid and lightweight plastic material. Housing portion 10a includes a Galilean optical system with one or more objective lenses 16 mounted in housing 10a adjacent the distal open end 12 The objective lens(es) 16 may include, but are not limited to, convex, biconvex, plus convex, doublet piano-convex, doublet bi-convex, double convex crown and concave flint, and other suitable precision magnification lenses.

According to an aspect of the invention, there may be one, two, or three objective lenses 16 present. The device 100 illustrated in FIG. 1 includes two lenses that are coupled together to form the objective lens 16. The resulting achromat lens 16 minimizes chromatic aberration. According to an aspect of the invention, the objective lens(es) 16 may be substantially rectangular. When a rectangular objective lens 16 is employed, a wider field of view is obtained, as more light is allowed to enter the device. According to another aspect of the invention, the objective lens(es) 16 may be substantially circular.

Still referring to FIG. 1, the Galilean optical system further includes one or more eye lenses 18 mounted in housing portion 10b adjacent the proximal end 14 thereof. The eye lens(es) 18 may include, but are not limited to, concave, biconcave, piano-concave, negative, diverging, and other suitable precision magnification lenses. According to an aspect of the invention, the eye lens(es) 18 may be bi-concave, or negative.

Figure 2:
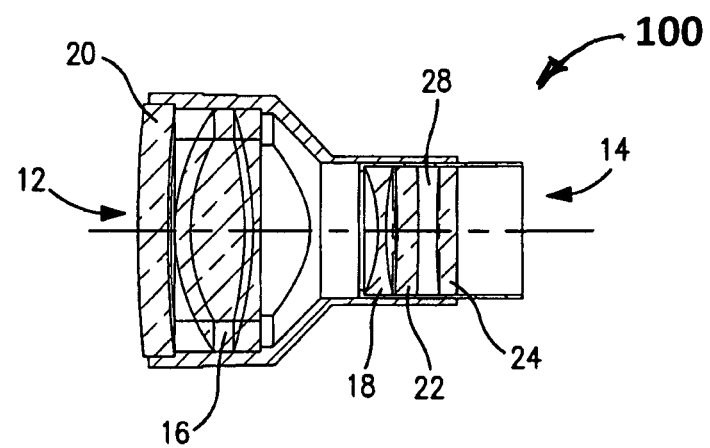
FIG. 2 is a cross-sectional, assembled view of the device illustrated in FIG. 1.

The magnification device 100 illustrated in the exploded view of FIG. 1 is shown assembled in FIG. 2. As needed, a lens 24, for spectacle correction may be present in the device 100 and mounted in housing portion 10b adjacent the proximal end 14. To the extent a spectacle correction lens is unnecessary, the lens 24 is plano. Regardless of which type of lens 24 is included in the device 100, the spectacle correction or plano lens closes the proximal end 14 of the housing portion 10b. Lenses 16, 18, and 24 and filters 22 and 20 are mounted in the housing with an epoxy or other suitable adhesive.

Figure 3:
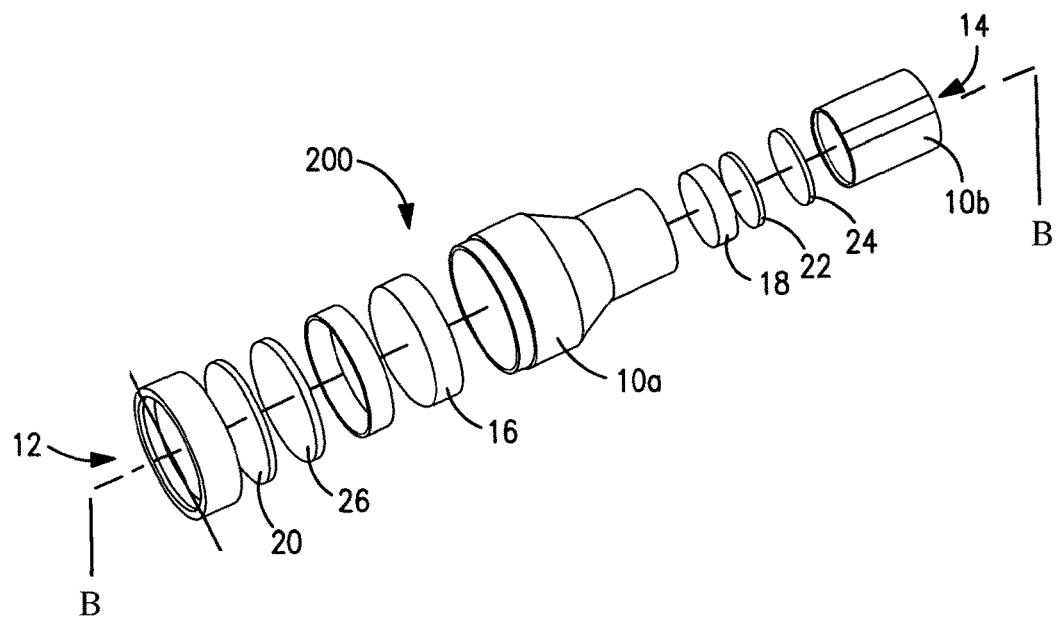
FIG. 3 is an exploded perspective view of a second embodiment of a magnification device according to an aspect of the invention.
Figure 4:
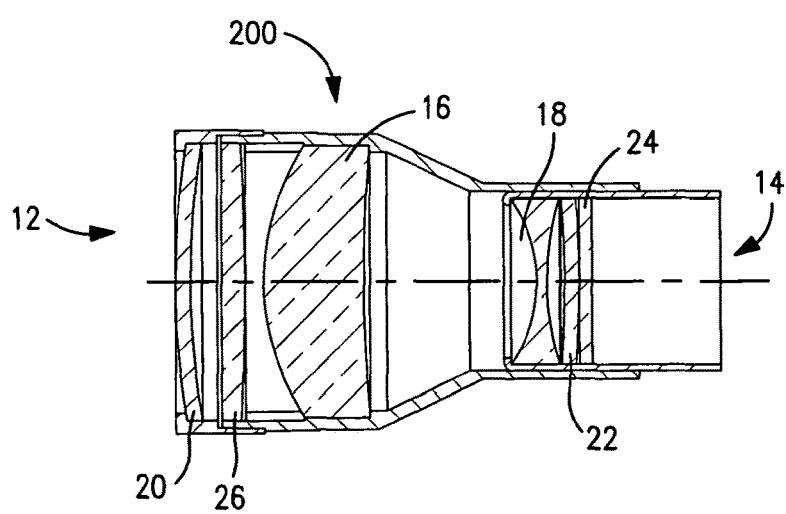
FIG. 4 is a cross-sectional, assembled view of the device illustrated in FIG. 3.

Referring to FIG. 3, a magnification device 200 according to a second aspect of the invention is illustrated. In this aspect, a working distance lens 26 is included in the device 200, which is further illustrated in an assembled state, in the cross-sectional view of FIG. 4, taken along lines B-B of FIG. 3.

Lenses having magnification, i.e., collecting optics, produce an increase in energy or power density, as the beam diameter is reduced by the magnifying power of the optics, which, when viewing a laser beam through the lenses, may increase and result in hazardous exposure conditions to the eye. Although some laser systems are incapable of producing hazardous exposure conditions during normal operation, when viewing a beam through an optical instrument, for example, an eye-loupe, the hazards may be increased. In the optical systems of the magnification devices described herein, which collect light through the objective lens(es) 16, the hazards from lasers are magnified, and can easily damage a person's vision since the cornea and lens focus the laser energy onto the retina. When viewing the laser from within the beam (intrabeam viewing) the hazard may be increased by as much as the square of the magnifying power of the optical magnification device.

Advantageously, the filtering system according to the invention blocks or filters the harmful transmission of electromagnetic radiation prior to becoming collected and increased by the optical system, and prior to entering the objective lens(es) 16, while being transparent to maximize visible light transmission. The filtering system, as illustrated in FIG. 1, includes an exterior first filter lens 20 mounted to the distal open end 12 of the housing 10a. The exterior filter lens 20 closes the distal open end 12 of the housing 10a. The exterior filter lens 20 advantageously attenuates the electromagnetic radiation to a safe level, but some radiation is still transmitted through the device. As the remnants of radiation are transmitted through the optical system, the remnants are magnified to a level that may become dangerous. To attenuate the remaining radiation that has become magnified by passing through the optical system, the filtering system also includes a second filter lens 22 mounted adjacent to the proximal open end 14 of housing 10b. The second filter lens 22 of the filtering system is provided in the interior of the housing 10b to eliminate any possibility of harmful radiation reaching the user's eyes through any of the lenses (objective or eye lens(es)) of the magnification device.

The type of filters suitable for use according to the invention depend upon the radiation-emitting device being used during a procedure. For example, to prevent damage from a laser transmitting beams at wavelengths ranging between about 2600 to about 3000 nm would require a filtering system that blocks wavelengths in the above-described range. There are many different types of lasers available on the market suitable for use, some of which are capable of emitting more than one wavelength. Examples of lasers include, but are not limited to: argon fluoride, xenon chloride, xenon fluoride, helium cadmium, argon, excimer, erbium-yttrium-aluminum-garnet (Er:YAG), neodymium:yttrium-aluminum-garnet (Nd:YAG), erbium:chromium:yt-triumscandium-gallium-garnet (ER:CR:YSGG), laser diodes, titanium-sapphire, ruby, alexandrite, erbium, hydrogen fluoride, and carbon monoxide and dioxide.

Depending upon the laser used, the application, and the manner in which the laser is used, a protection factor, i.e. the Optical Density (OD), is calculated with respect to the filter(s). The higher the OD factor, the higher the attenuation. Filters suitable for use according to the invention are available from NoIR Laser Company, L.L.C. of South Lyon, Mich. and/or Honeywell Safety Products, Smithfield R.I. The filters 20 and 22 may suitably be formed of polycarbonate.

Figure 5:
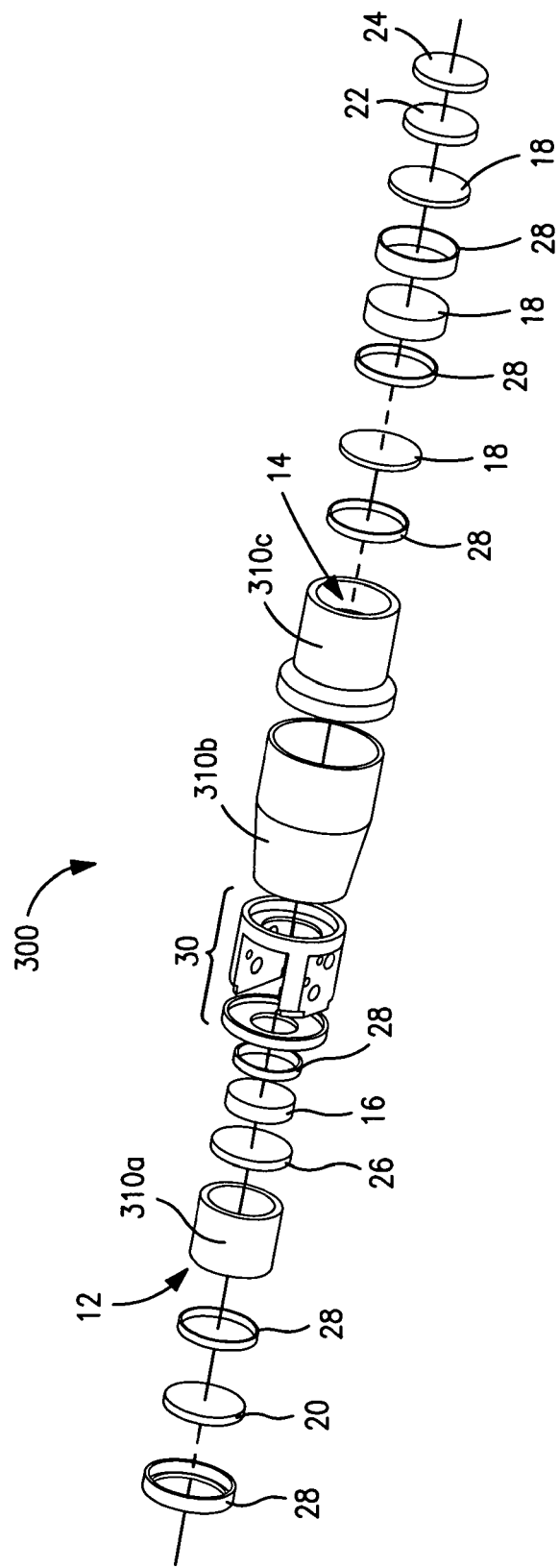
FIG. 5 is an exploded perspective view of a magnification device according to another aspect of the invention.

FIG. 5 illustrates a magnification device 300 according to another aspect of the invention. In this aspect, a Keplerian optical system is employed to provide a wider field of view than the Galilean system, which has a relatively small field of view. The Galilean system, however, is lighter in weight than the Keplerian. The housing for the optical and filtering system includes three separate housing portions, 310a, 310b and 310c. The three housing portions are provided to allow for the precise placement of the objective lens(es) 16, the prism assembly 30, and the eye lens(es) 18 prior to assembly.

As with devices 100 and 200, the filtering system includes an exterior filter lens 20 mounted to the distal open end 12 of the housing 310a. The filter lens 20 closes the distal open end 12 of the housing 310a. The filtering system also includes a second filter lens 22 mounted adjacent to the proximal open end 14 of housing 310c. A prescription or plano lens 24 is mounted to and closes the proximal open end 14 of housing portion 310c. As described above, the second filter lens 22 is provided to ensure that no harmful radiation reaches the user's eyes through any of the lenses (objective or eye lens(es)) of the magnification device.

In this aspect, spacers 28 are used to separate the various lenses 16 and 18. For example, a spacer 28 is illustrated in FIG. 5 between the housing 310a and the exterior filter lens 20. Additional spacers 28 are illustrated between the eye lenses 18. The spacers 28, which may suitably be formed of plastic, provide for proper placement and retention of the lenses 16, 18 and 20 within the housing portion 310a and housing portion 310c. A working distance lens 26 may also be present in the device.

In the Keplerian optical system, the one or more objective lenses 16 may be substantially circular, or could be rectangular, and may include, but are not limited to, convex, biconvex, plus convex, doublet piano-convex, doublet biconvex, and other suitable precision magnification lenses. The device 300 illustrated in FIG. 5 includes three eye lenses 18. In this aspect of the invention, one or more of the eye lenses 18 are positive, convex, or bi-convex or achromat.

Figure 6:
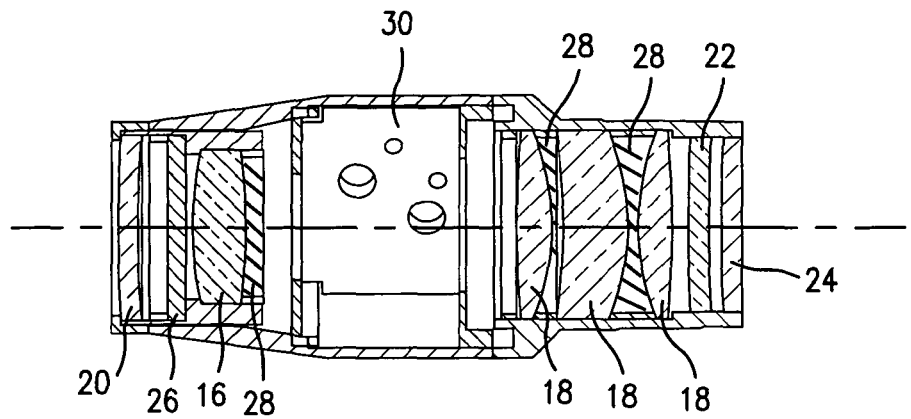
FIG. 6 is a cross-sectional view of the device illustrated in FIG. 5.
Figure 7:
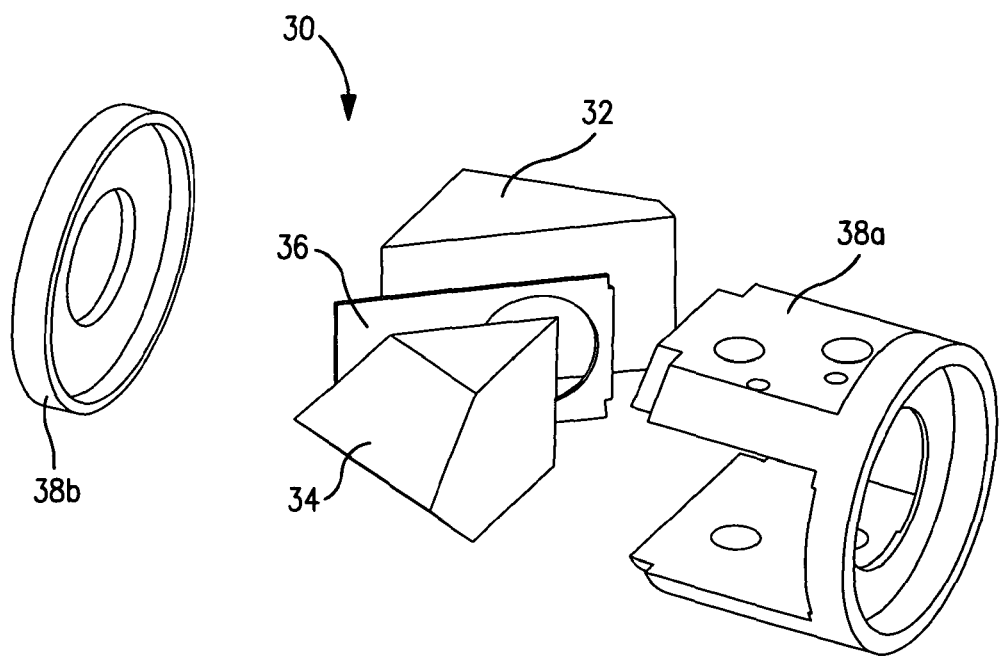
FIG. 7 is an exploded view of a prism assembly illustrated in FIG. 5.

The device 300 of FIG. 5 is illustrated in FIG. 6 in an assembled state. The prism assembly 30 illustrated in FIG. 5 is illustrated in further detail in FIG. 7. In FIG. 7, the prism assembly 30 includes an Amici prism 32 and a Schmidt prism 34, separated by a divider 36, and disposed in a housing 38a and 38b. The apertures formed in the housing 38a and 38b and in the divider 36 allow for the passage of light. Since the Keplerian optics employed in this aspect of the invention inverts the orientation of a viewed image or object, the prism assembly 30 is provided to invert the viewed object so that it appears in the correct context to preserve the field of view.

Figure 8:
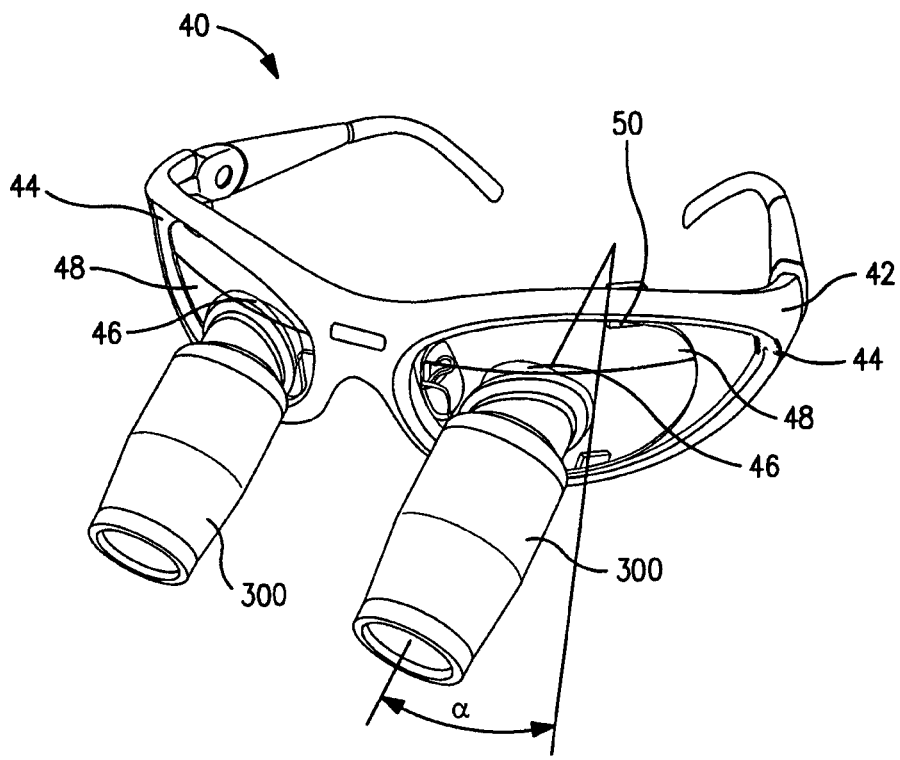
FIG. 8 is a front elevational view of an assembly illustrating magnification devices in a carrier device.
Figure 9:
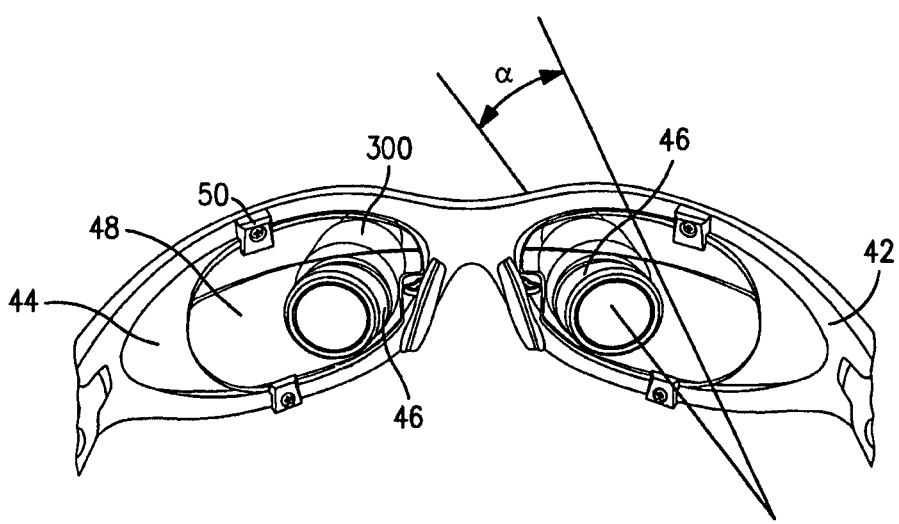
FIG. 9 is a rear elevational view of the assembly illustrated in FIG. 8.

Referring now to FIGS. 8 and 9, magnification devices or loupes according to an aspect of the invention are illustrated as being disposed in a carrier device 40 to provide binocular vision to a user. The carrier device 40 in this aspect is a spectacle or an eyeglass frame 42 with carrier lenses 44. Alternative carrier devices 40 may include headbands, goggles, visors, or other devices suitable for supporting the magnifying devices to provide binocular vision. The carrier lenses 44 each include an aperture 46 through which the magnification devices 100, 200, or 300 are mounted. The carrier lenses 44 may be plano or prescription, and are configured for preventing the harmful transmission of radiation as with filter lenses 20 and 22. Additional supporting spectacle lenses 48 may be secured to the spectacle frame 42 by a clip 50 or other conventional means. Although a Keplerian assembly according to an aspect of the invention is illustrated in FIGS. 8 and 9, it should be understood that a Galilean assembly may also be mounted on a spectacle frame 42 or other suitable carrier devices 40 as described above.

As illustrated in FIGS. 8 and 9, the magnification devices are positioned in the carrier lenses at a selected angle of declination (a) to provide a user with ease of use, and to promote proper posture for the back, neck, head, and eyes that may be assumed when working at a close distance.

According to an aspect of the invention, the filtering system attenuates wavelengths from a radiation-emitting source, for example, a laser, in the range of about 190 to about 400 nm. In another aspect, the filtering system attenuates wavelengths in the range of about 730 nm to about 760 nm, in the range of about 785 nm to about 1090 nm, and in the range of about 2700 nm to about 2950 nm. According to another aspect of the invention, the filtering system attenuates wavelengths at about 10600 nm. It should be understood that additional wavelengths may be filtered, as the above ranges of wavelengths is not meant to be exhaustive.

Advantageously, the magnification devices according to the invention block, or attenuate harmful wavelengths of radiation, including laser light, whether visible or invisible, and provide magnification at a one or more of a plurality of magnifications (e.g., 2.5×, 3.5×, 4.5×, and 6.0×). It should be understood that other magnifications may also be provided.

As the different magnification levels provide different degrees of amplification of the reflected laser light, the optical density of the filters 20 and 22 require adjustment as a function of the magnification level. For example, a magnification level of 2.5×, may require a filter optical density of at least 5, whereas a magnification level of 6.0×, may require a filter optical density of at least 6, to provide adequate filtering capability to prevent damage to the eye caused by the reflected laser light.

The optical density of absorptive filters may be determined by an amount of filtering material that is introduced into the base material (e.g., glass, plastic, polycarbonate, etc.). The filtering material may be selected to absorb one or more undesired wavelengths, while allowing other wavelengths to pass through.

Absorptive filters of optical density 5 or greater are known in the art. For example, the filter number 109 manufactured by Honeywell, Co., is an example of an absorptive filter having an optical density of 5 that is suitable for use as filter 20 in the device shown in FIG. 1. For absorptive filters of optical density 6, the absorptive filter may be manufactured using a thicker base material and/or greater concentration of filtering material. However, as the optical density increases, the cost of manufacture and the filter weight increases. In addition, the amount of light in a desired visible wavelength range reaching the eye decreases; causing the image being viewed to be darker.

In one aspect of the invention, a plurality of absorptive filters may be used as the filter 20 in the device shown in FIG. 1, wherein each of the plurality of absorptive filters has an optical density less than the required density value. However, the combined filtering effect of the plurality of absorptive filters achieves the required (or desired) optical density. For example, two absorptive filters, each having an optical density 3 may be used as the filter 20 in the device shown in FIG. 1, to achieve an optical density of at least 5. Determination of, optical densities of individual ones of the plurality of absorptive filters to achieve a desired combined optical density is determinable, without undue experimentation. Hence, the use of one or more absorptive filters, each having an optical density less than a desired optical density has been contemplated and considered within the scope of the invention claimed.

In addition, as absorptive filter properties are generally additive, the placement of the absorptive filter(s) may be distributed to provide a clearer image of the object being viewed. In one aspect of the invention, one absorptive filter, having a first optical density, may be positioned at the distal end of housing 10*a*, and a second absorptive filter, having a second optical density, may be positioned at the proximal end of housing 10*b*. In this manner, the optical densities of the filters at the distal and proximal ends may be the same or different so that the combination of the absorptive filters achieves a combined desired optical density.

Reflective filters, on the other hand, are manufactured by depositing a reflective coating on a base material (i.e., glass, plastic polycarbonate). The reflective coating may reflect one or more desired wavelengths while allowing other wavelengths to pass through un-attenuated (or with limited attenuation). A dielectric glass filter manufactured by Honeywell, Co., having an optical density of 5 is known in the art.

However, the thickness of the reflective coating does not determine the reflective properties of the filter. Thus, in the one aspect of the invention, wherein more than one reflective filter is used, the optical densities of the individual filters may be selected to achieve a combined desired optical density. Determination of optical densities of individual reflective filters to achieve a desired combined optical density is determinable without undue experimentation. Hence, the use of one or more reflective filters, each having an optical density less than a desired optical density, has been contemplated and considered within the scope of the invention claimed. Hence, a plurality of reflective filters, each having an optical density less than a desired optical density may be selected as filter 22, shown in FIG. 1.

As would be appreciated, the desired optical density of the absorptive lens 20 and the reflective lens 22 may be the same or different.

In another aspect of the invention, using multiple absorptive and reflective filters, the filter lens arrangement may be selected to provide a desired absorption/reflective capability of selected wavelengths while providing maximum throughput of the remaining (unabsorbed/unreflected) wavelengths.

Figure 10:
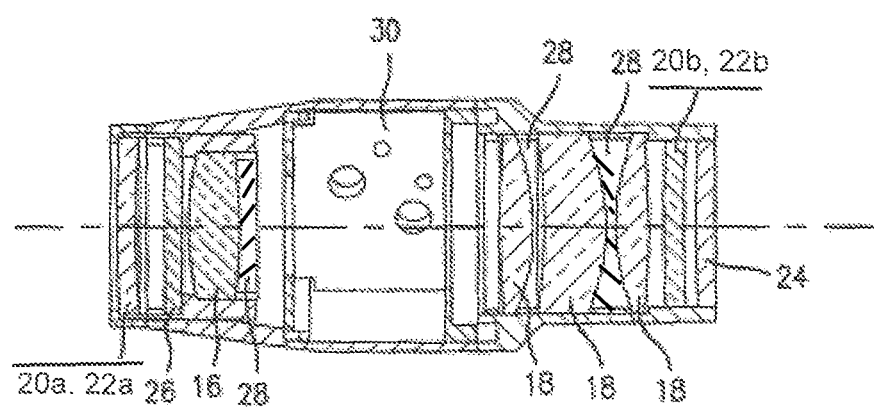
FIG. 10 is a cross-sectional view of a magnification device in accordance with a second embodiment of the invention.

FIG. 10 illustrates an exemplary magnification device in accordance with an aspect of the invention, wherein two absorptive filters and two reflective filters are used to achieve a desired combined optical density. In this illustrative embodiment, a first absorptive filter 20*a*, having a known optical density, absorbs light energy at at least one wavelength (e.g., 800, 810, 940, 980, 1064) and a first reflective filter 22*a*, having a known optical density, reflects light energy at at least one wavelength (e.g., 2780, 2940, 10600) are positioned in front of the objective lens 16.

The light energy remaining after absorption and reflection by the combined filter lens 20*a* and 22*a*, traverses the magnification system, (i.e., objective lens(es) 16 and eyelens(es) 18), wherein the remaining light energy is amplified based on the magnification level of the magnification system. Wavelengths (e.g., 800, 810, 940, 980, 1064) of the magnified remaining light are filtered by a second absorptive filter 20*b*, behind the eye lens 18. The second absorptive filter 20*b* may have an optical density similar to or different from the optical density of the first absorptive filter 20*a*. Similarly, the magnified remaining unabsorbed light energy is applied to a second reflective filter 22*b*, which is positioned behind the eye lens, wherein selected wavelengths (e.g., 2780, 2940, 10600, etc.) are reflected. The second reflective filter 22*b* may have an optical density similar to or different from the optical density of the first reflective filter 22*a*. In this case, the optical densities of the individual absorptive filters combine to achieve a desired optical density and the optical densities of the individual reflective filters combine to achieve a second desired optical density.

Although, FIG. 10 illustrates an exemplary magnification device in accordance with the principles of the invention, it would be recognized that other positions or orientations of the plurality of absorptive and reflective filters may be achieved and, have been contemplated and considered within the scope of the invention. For example, at least two absorptive filters may be positioned at the distal end of housing 10*a* while two reflective filters may be positioned at the proximal end of housing 10*b*—each having an optical density less than a desired corresponding optical density. In another configuration, two absorptive and one reflective filter may be positioned at the distal end of housing 10*a* and one reflective filter may be positioned at the proximal end of housing 10*b*. Other combinations of a number of filters (absorptive/reflective) and the placement of theses filters have been considered and considered within the scope of the invention claimed.

In one aspect of the invention, absorptive filter 20 (FIG. 1) may possess absorptive properties at one or more wavelengths. In one embodiment of the invention, the absorptive filter 20, may provide filtering (i.e., high absorption) at one or more wavelengths selected from a group comprising 800 nm, 810 nm, 940 nm, 980 nm and 1064 nm. Similarly, reflective filter 22 (FIG. 1) may possess reflective filtering properties (i.e., high reflectivity) at at least one wavelength selected from a group comprising 2780 nm, 2940 nm, and 10600 nm.

Although the invention disclosed herein discusses specific wavelengths that are produced with currently available lasers, it would be recognized that the specific wavelengths absorbed and/or reflected may be changed and/or added to without altering the scope of the invention. In addition, it would be known in the art that the specific wavelengths discussed herein represent a band of wavelengths centered on the wavelengths presented herein to account for divergence of the wavelength generated by the laser caused during the generation of the laser and/or the operation of the laser, wherein the laser light generated is represented as a nominal value.

The invention has been described with reference to specific embodiments. One of ordinary skill in the art, however, appreciates that various modifications and changes can be made without departing from the scope of the invention as set forth in the claims. Accordingly, the specification is to be regarded in an illustrative manner, rather than with a restrictive view, and all such modifications are intended to be included within the scope of the invention.

Benefits, other advantages, and solutions to problems have been described above with regard to specific embodiments. The benefits, advantages, and solutions to problems, and any element(s) that may cause any benefits, advantages, or solutions to occur or become more pronounced, are not to be construed as a critical, required, or an essential feature or element of any or all of the claims.

What is claimed is:

1. A vision enhancing assembly, comprising:
a carrier device;
one or more magnification devices coupled to the carrier device, each of said magnification devices comprising:
a housing comprising a distal open end and a proximal open end;
an optical system comprising at least one objective lens mounted in said housing adjacent said distal open end and at least one eye lens mounted in said housing adjacent said proximal open end, said optical system achieving a desired level of magnification; and
a filtering system comprising:
an absorptive filter system comprising:
a first absorptive lens mounted adjacent, and external, to said distal open end, and
a second absorptive lens mounted adjacent, and external, to said proximal open end, said absorptive filter system configured to:
attenuate a first set of wavelengths, wherein an optical density of said first absorptive lens and an optical density of said second absorptive lens are selected to achieve an optical density, for said absorptive filter system, based on said desired level of magnification of said optical system; and
a reflective filter system comprising:
a first reflective lens mounted adjacent, and external, to said distal open end, and
a second reflective lens mounted adjacent, and external to said proximal open end, wherein an optical density of said first reflective lens and an optical density of said second reflective lens are selected to achieve an optical density for said reflective filter system based on said desired level of magnification, said reflective filter system configured to:
attenuate a second set of wavelengths, wherein wavelengths within said first set of wavelengths are different than wavelengths in the second set of wavelengths.

2. The vision enhancing assembly according to claim 1, wherein said carrier device is an eyeglass frame with carrier lenses.

3. The vision enhancing assembly according to claim 1, wherein at least one of said at least one objective lenses is convex.

4. The vision enhancing assembly according to claim 1, wherein at least one of said at least one objective lenses is substantially rectangular.

5. The vision enhancing assembly according to claim 1, wherein at least one of said at least one objective lenses is substantially circular.

6. The vision enhancing assembly according to claim 1, wherein said optical system is Galilean.

7. The vision enhancing assembly according to claim 6, wherein at least one of said at least one eye lens is concave or negative.

8. The vision enhancing assembly according to claim 1, wherein said optical system is Keplerian.

9. The vision enhancing assembly according to claim 8, wherein at least one of said at least one eye lens is convex or plus.

10. The vision enhancing assembly according to claim 1, wherein said optical system further comprising:
a spectacle correction lens mounted in said housing adjacent said proximal open end.

11. The vision enhancing assembly according to claim 1, wherein said first absorptive lens comprises:
a plurality of absorptive lenses, each of said plurality of absorptive lenses having an optical density less than said optical density of said absorptive filter system, and
said second absorptive lens comprises:
a plurality of absorptive lenses, each of said plurality of absorptive lenses having an optical density less than said optical density of said absorptive filter system,
wherein a combined optical density of said plurality of absorptive lenses of said first absorptive lens and said plurality of absorptive lenses of said second absorptive lens is at least equal to said optical density of said absorptive filter system.

12. The vision enhancing assembly according to claim 11, wherein said plurality of absorptive lens of said first absorptive lens are positioned in front of said at least one objective lens and said plurality of absorptive lens of said second absorptive lens are positioned behind said at least one eye lens.

13. The vision enhancing assembly according to claim 11, wherein said first reflective lens comprises:
a plurality of reflective lenses, each of said plurality of reflective lenses having an optical density less than said optical density of said reflective filter system; and
said second reflective lens comprises:
a plurality of reflective lenses, each of said plurality of reflective lenses having an optical density less than said optical density of said reflective filter system
wherein a combined optical density of each of said plurality of reflective lenses of said first reflective lens and said plurality of reflective lens of said second reflective lens is at least equal to said optical density of said reflective filter system.

14. The vision enhancing assembly according to claim 13, wherein said plurality of reflective lens of said first reflective lens are positioned in front of said at least one objective lens and said plurality of reflective lens of said second reflective lens are positioned behind said at least one eye lenses.

15. The vision enhancing assembly according to claim 13, wherein said optical density of said first absorptive lens and said optical density of said second absorptive lens are selected from a group consisting of: same and different.

16. The vision enhancing assembly according to claim 1, wherein said optical density of said first reflective lens and said optical density of said second reflective lens are selected from a group consisting of: same and different.

* * * * *